United States Patent [19]

Stroetmann et al.

[11] Patent Number: 5,658,318

[45] Date of Patent: Aug. 19, 1997

[54] METHOD AND APPARATUS FOR DETECTING A STATE OF IMMINENT CARDIAC ARRHYTHMIA IN RESPONSE TO A NERVE SIGNAL FROM THE AUTONOMIC NERVE SYSTEM TO THE HEART, AND FOR ADMINISTRATING ANTI-ARRHYTHMIA THERAPY IN RESPONSE THERETO

[75] Inventors: Brigitte Stroetmann; Konrad Mund, both of Uttenreuth; Siegfried Kallert, Erlangen, all of Germany

[73] Assignee: Pacesetter AB, Solna, Sweden

[21] Appl. No.: 534,933

[22] Filed: Sep. 28, 1995

[51] Int. Cl.$^6$ .................................................. A61N 1/39
[52] U.S. Cl. ................................................................ 607/6
[58] Field of Search ........................ 128/642, 675, 128/700, 705; 607/17, 18, 23, 118, 6

[56] References Cited

U.S. PATENT DOCUMENTS

| | | | |
|---|---|---|---|
| 3,157,181 | 11/1964 | McCarty | 607/118 |
| 3,240,207 | 3/1966 | Barker et al. | 128/675 |
| 4,201,219 | 5/1980 | Bozal-Gonzales | 607/22 |
| 4,791,931 | 12/1988 | Slate | 607/23 |
| 4,917,092 | 4/1990 | Todd et al. | |
| 5,111,815 | 5/1992 | Mower | 607/6 |
| 5,203,326 | 4/1993 | Collins | |
| 5,243,980 | 9/1993 | Mehra | |
| 5,318,592 | 6/1994 | Schaldach | |
| 5,522,854 | 6/1996 | Ideker et al. | 607/6 |

FOREIGN PATENT DOCUMENTS 0565909  10/1993  European Pat. Off. .

OTHER PUBLICATIONS

"Clinical Experience with a Helical Bipolar Stimulating Lead," Tarver et al., PACE, vol. 15 Oct. 1992, pp. 1545–1556.

"Reestablishment of Physiological Regulation —A Challenge to Technology" Schaldach, Electrotherapy of the Heart, 1992, pp. 209–214.

Primary Examiner—William E. Kamm
Attorney, Agent, or Firm—Hill, Steadman & Simpson

[57] ABSTRACT

A device for detecting a state of imminent cardiac arrhythmia, relative to a normal state for a heart, in response to activity in nerve signals conveying information from the autonomic nerve system to the heart, contains a sensor body for sensing neural activity, a comparator with a threshold value forming a condition for the presence of an arrhythmia, the comparator emitting an arrhythmia-indicating output signal depending on whether neural activity meets the condition, and the sensor body being placeable in an extracardiac position for at least one of the sympathetic and vagus nerves. The sensor body directly senses activity in the nerve at that location in direct contact with the nerve. An implanted blood pressure sensing cuff also can be provided which generates signals indicative of blood pressure which can be evaluated in combination with the nerve signals for identifying the state of imminent cardiac arrhythmia.

14 Claims, 3 Drawing Sheets

METHOD AND APPARATUS FOR DETECTING A STATE OF IMMINENT CARDIAC ARRHYTHMIA IN RESPONSE TO A NERVE SIGNAL FROM THE AUTONOMIC NERVE SYSTEM TO THE HEART, AND FOR ADMINISTRATING ANTI-ARRHYTHMIA THERAPY IN RESPONSE THERETO

BACKGROUND OF THE INVENTION

1. Field of the Invention

The present invention is directed to a method and apparatus for detecting a state of imminent cardiac arrhythmia, wherein detection of the state of imminent arrhythmia is made by using nerve signals from the autonomic nerves innervating the heart, and for administering appropriate anti-arrhythmia therapy upon detection of the state of imminent cardiac arrhythmia.

2. Description of the Prior Art

In the control of a device for heart therapy, such as a pacemaker, it is known to use signals providing a measure of the body's work load, in addition to utilization of the parameters in the ECG signal generated by the heart itself. These signals can be obtained when one or more load-related physiological variables, such as pH, oxygen saturation in blood etc., is/are detected with sensors. In more advanced devices for heart therapy, in which the device is able to provide many kinds of treatment depending on the condition of the heart, control of the device can also be exercised by utilization of other signals indicative of whether such conditions are either present, or are in the process of becoming established (incipient). Signals of these kinds can be related to hemodynamic conditions, e.g. blood pressure in the right ventricle. A sudden drop in pressure, combined with a very fast heart rate, could be indicative of, e.g., fibrillation in the heart.

In particular, control can be exercised through signals containing information related to the autonomic nervous system (ANS). In addition to being indicative of established heart conditions, these signals can also improve the possibility of detecting impending changes in the heart's condition so that prophylactic treatment can be started, e.g. to prevent the development of tachyarrhythmias, fibrillation in particular.

The autonomic nervous system innervates the heart by means of two sub-systems, the sympathetic nervous system and the parasympathetic nervous system respectively. The sub-systems will henceforth usually be referred to simply as the "sympathetic nerve" and "vagus nerve", unless otherwise specified. Increased signal activity in the sympathetic nerve increases heart activity, and increased signal activity in the vagus nerve reduces heart activity. Both systems normally balance each other when the body is at rest.

European Application 0 532 144 discloses a system for ANS control of a device for heart therapy. The device can also include a nerve stimulator, in addition to a conventional device for electrical heart therapy. In order to achieve a control signal related to the ANS, activity is detected in the sympathetic nerve by measurement of the regional, effective rise in impedance in the right ventricle. After the measurement signal is processed, the rise in impedance can be used as the control signal for the therapy device. Control could also be exercised through collaboration with one or more of the signals indicative of the body's work load, as noted above. In the device according to European Application 0 532 144, the activity of the sympathetic nerve or the activity of the nerve signal is indirectly sensed by measurement of this activity in the form of its effect on the heart via some appropriate parameter.

When the activity of the nerve signal is measured indirectly, the measurement becomes dependent on the ability of the measurement parameter to simulate the activity. If the patient suffers from some heart disease, which in particular may occur among patients in need of a heart therapy implant, this is not the case, and measurement in the heart will not then supply correct information about the activity of the nerve signal.

In addition to indirect measurement of the activity of the sympathetic nerve according to European Application 0 532 144, stimulation of the vagus nerve, more particularly its endocardiac ends, during impending tachyarrythmia has also been proposed (Max Schaldach "Electrotherapy of the Heart", 1992, Springer Verlag, Heidelberg, pp. 210–214).

In other electromedical therapy, e.g. the treatment of epilepsy, it is known to directly stimulate a nerve, more particularly the vagus nerve, by means of an implantable pulse generator. One such system having a helical electrode applied to the vagus nerve in the neck area is described in an article by Tarver et al.: "Clinical Experience with a Helical Bipolar Stimulating Lead", Pace, Vol. 15, October, Part II 1992, pp. 1545–1566. This system, however, only stimulates the nerve, and the pulse generator is controlled by means of an extracorporeally applied magnet.

SUMMARY OF THE INVENTION

It is an object of the present invention to provide a method and an apparatus for detecting a state of imminent cardiac arrhythmia, and for administering appropriate anti-arrhythmia therapy which avoids the above-discussed disadvantages of known devices and methods.

The above object is achieved in accordance with the principles of the present invention in a method and apparatus for detecting a state of imminent cardiac arrhythmia in response to activity in a nerve signal conveying information from the autonomic nerve system to the heart, by sensing neural activity of at least one of the sympathetic and vagus nerves using a sensor body placed in an extracardiac position for directly sensing such neural activity, with the sensed signal being supplied to a comparator which has a threshold value that defines a condition for the presence of arrhythmia. The comparator emits an imminent arrhythmia-indicating output signal depending on whether the sensor signal, representing the neural activity, meets the condition established by the comparator threshold. The sensor body may be placed for directly sensing the aforementioned neural activity in direct contact with the sympathetic and possibly vagus nerves.

The invention is described in greater detail with reference to an embodiment as disclosed in the attached drawings of a device according to the invention for heart therapy as applied in the above-described AICD defibrillator system. For illustrative—not restrictive—reasons, the device according to the invention will henceforth be designated in this description as a "nerve-stimulating heart defibrillator" or a "nerve-heart defibrillator" whose task is to terminate fibrillation in the heart. It is to be understood that also other tachyarrhythmias, such as impending but as yet unestablished fibrillation treated with ATP or cardioversion according to conventional techniques, can be treated and that the designation "nerve-heart defibrillator" in this context is a term only employed for explanatory purposes. Although the nerve-heart stimulator is explained and described herein in conjunction with a AICD-type defibrillator system, it is further understood that the nerve-heart stimulator can be employed independently without all the parts in the described defibrillator system.

DESCRIPTION OF THE PREFERRED EMBODIMENTS

Figure 1:
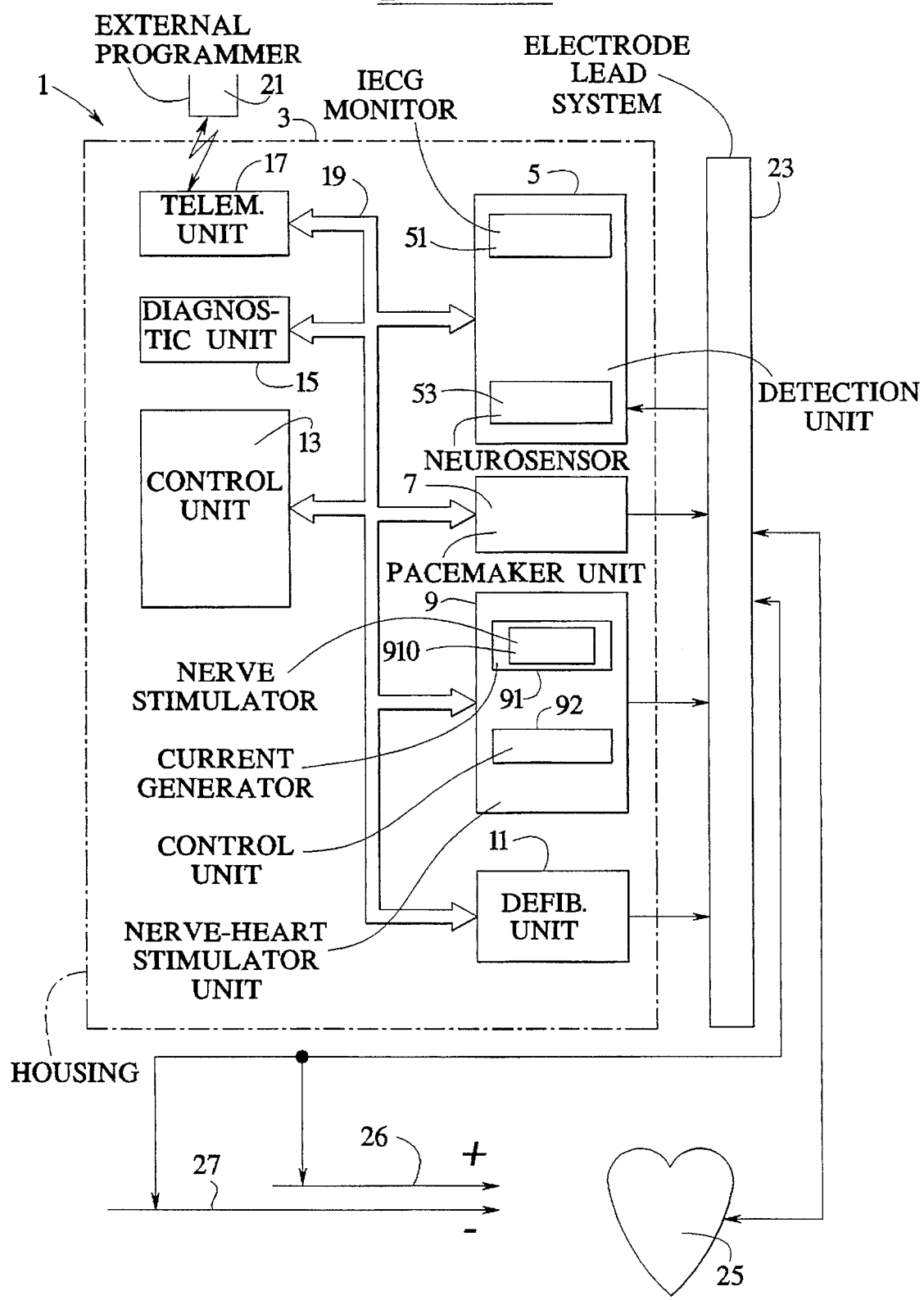
FIG. 1 is a block diagram of a defibrillator system, embodying a nerve-heart defibrillator according to the invention.

FIG. 1 shows an example of a defibrillation system using the nerve-heart defibrillator according to the invention, in which defibrillator implant is generally referenced 1. The implant 1 has an enclosure which may consist of e.g. a titanium capsule 3. The implant 1 includes a detection unit 5, a pacemaker unit 7, which can emit stimulation pulses to the heart both in the case of bradycardia and in the case of tachycardia, a nerve-heart defibrillation unit 9, an electrical defibrillation unit 11, a control unit 13, a diagnosis unit 15 and a telemetry unit 17. The different units in the implant 1 communicate internally via a databus 19.

The implant 1 communicates with an external programmer 21 via the telemetry unit 17, whereby communications primarily include the transmission of programming data to the implant 1 and transmission of diagnostic data, e.g. about different events in the heart, sensor signals and ECG signals, from the diagnostic unit 15.

Figure 5:
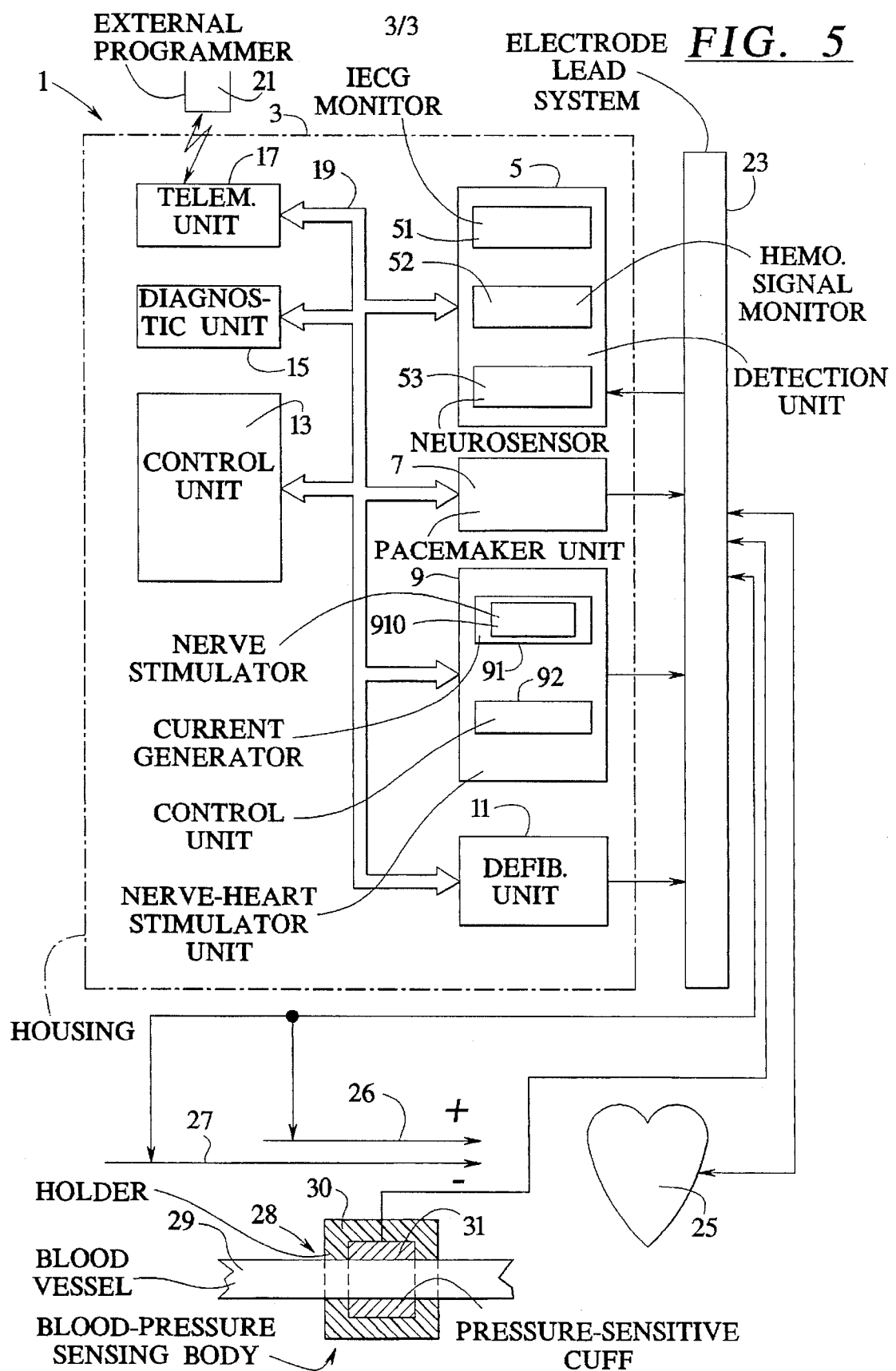
FIG. 5 is a block diagram of a further embodiment of a defibrillator system, embodying a nerve-heart defibrillator according to the invention.

The implant 1 is connected to a heart 25 via an electrode lead system 23 of attendant electrodes for emitting pacing as well as defibrillation pulses (including pulses with somewhat less energy than the level required for defibrillation, e.g. cardioversion pulses) to the heart 25 and for picking of signals indicative of the heart's condition. It should be noted that FIG. 1 is only schematic, and the signals designating the heart's condition also encompass sensor signals obtained from the sensing of heart-related physiological variables elsewhere in the body, e.g. hemodynamics (pressure/flow) in the vascular system. As shown (enlarged) in FIG. 5, a blood pressure-sensing body 28 can be arranged, for example, in the patient's neck area around a blood vessel 29 (neck artery or vein), whereby the sensing body 28 may consist of a ring-shaped (possibly suturable) holder 30 and a sensing device on the inside of the holder device in the form of a pressure-sensitive cuff 31. The sensing body 28 supplies hemodynamic signals indicative of a blood pressure to the detection unit 5.

The implant 1 is also in connection with the sympathetic nerve 26 (a plus sign designates an activating effect on heart activity) and the vagus nerve 27 (a minus sign designates an inhibitory effect on heart activity) via the system 23 of electrodes and electrode leads in order to emit nerve-stimulating pulses to the vagus nerve 27 and blocking current to the sympathetic nerve 26 and for picking up heart-related nerve signals therefrom.

The defibrillator implant 1 accordingly includes, in addition to the nerve-heart defibrillator unit 9 described below, circuitry for performing the functions found in a modern defibrillator (AICD) of the type noted above. Thus, the heart's condition is monitored in the detection unit 5 by means of an IECG-monitoring device 51 and (in the embodiment of FIG. 5) hemodynamic signal monitor. Heart-related nerve signals are also monitored in the detection unit 5 in a nerve signal-monitoring device or neurosensor 53. Such a sensor 53 may be formed by a comparator with a threshold value defining a condition for the presence of an arrhythmia. If sensed nervous activity meets the condition, the comparator issues an imminent arrhythmia-indicating output signal. Thus normal sinus rhythm and abnormal conditions in the heart, the latter possibly being bradycardia, hemodynamically unstable tachycardia and ventricular fibrillation requiring treatment, as well as nerve (sympathetic) signal activity indicating that the above conditions are established or impending, are detected in the detection unit 5.

Data from the detection unit 5 are sent to the control unit 13 which, depending on the data, orders a requisite therapy, such as tachycardia-terminating heart stimulation, and also sends a command signal to at least one of the units 7, 9 and 11. In the case of a determination that tachycardia-terminating stimulation is need, the command signal is sent to the pacemaker unit 7.

Except for the nerve-heart defibrillator unit 9 and parts of the detection unit 5 (the neurosensor 53 in particular), the above-described components and functions are conventional in nature, as noted above. They will henceforth thus only be considered to the extent they relate to the nerve-heart stimulator unit 9, which will now be described, and the neurosensor 53, to be described subsequently, in the following description.

The nerve-heart stimulator unit includes a current generator 91 for nerve stimulation and is capable of supplying nerve-activating pulsed current with a balanced average current level, e.g. with a frequency range of 20 to 50 Hz, a pulse amplitude of 0–9 V and a pulse width of 0.1–1 ms, from a nerve stimulator 910, in addition to nerve-blocking direct current/high-frequency current, to be discussed subsequently. The unit 9 further includes a time control unit 92 which is capable of supplying control information to the current generator 91 regarding e.g., which activating and blocking pulses, pulse sequences and continuous output signals should be delivered via the electrode system 23 from the unit 9 to the sympathetic nerve 26 and vagus nerve 27, respectively, and also when the pulses are to be emitted. It should also be noted that the pulses supplied from the unit 9 may additionally include other suitable forms of pulses, such as dual diphasic pulses and alternatingly biphasic pulses separated by a pulse interval. The operating parameters of the current generator 91 and of the time control unit 92 are, like other parameters in the implant 1, programmable via the telemetry unit 17. Therapy supplied from the unit 9 can be supplied, repeatedly if need be, over a period of time, e.g. 5 to 10 seconds, suitable to the therapy. The time control unit 92 is shown, merely for illustrative purposes, as a separate unit in the unit 9. It can naturally be an integrated part of the current generator 91.

Figure 2:
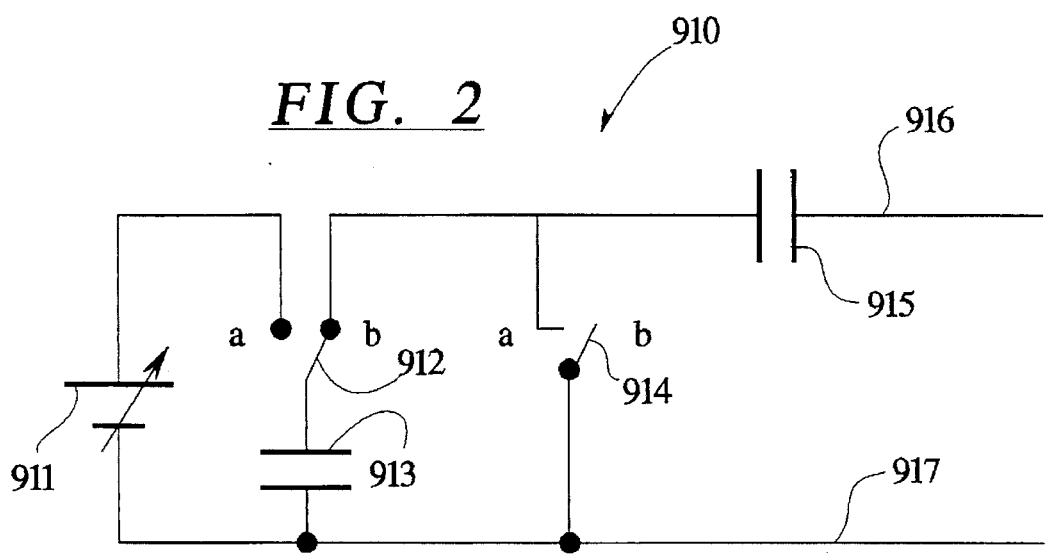
FIG. 2 shows an example of a vagus nerve stimulator in the nerve-heart defibrillator.

FIG. 2 shows an example of the nerve stimulator 910, which emits pulsed current for activating nerve stimulation, in the current generator 91. A voltage source 911 with a variable voltage V is connectable, via a switch 912, to a capacitor 913 with capacitance C. The capacitor 913 is also connectable, via the switch 912, to a capacitor 915, also with capacitance C. The capacitor 915 is connectable, via a switch 914, to an electrode output terminal 917. The nerve stimulator 910 can assume two states, a first state when the two switches 912 and 914 (both of which are controlled in parallel by the time control unit 92) assume the position marked in a FIG. 2, and a second state when the two switches 912 and 914 assume the position marked b. In the second state, the capacitors 913 and 915 are connected in series, whereupon the capacitor 913, which is charged to voltage V from the voltage source 911, is discharged via the capacitor 915 and the electrode output terminals 916 and 917. In the first state, the capacitor 913 is connected to the voltage source 911 by the switch 912, whereupon the capacitor 915 is also discharged via the electrode output terminals 916 and 917 and the patient. Control of events is exercised by the time control unit 92. The capacitance C for the capacitors 913 and 915 may, e.g., be 100 µF.

Figure 3:
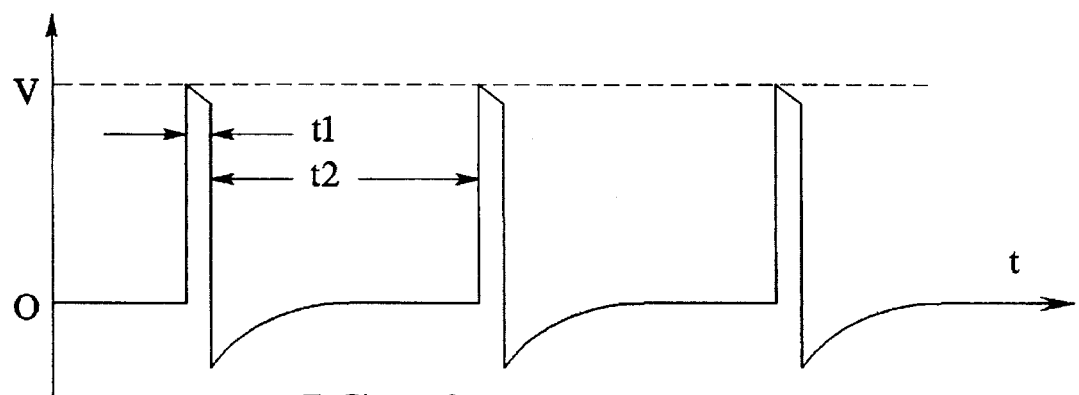
FIG. 3 shows illustrative examples of patterns of vagus nerve stimulation pulses generated in accordance with the invention.

Examples of pulses emitted by the unit 9 are shown in FIG. 3. FIG. 3 shows the output signal over time t between the electrode output terminals 916 and 917 in FIG. 2. The pulse width t1 may be 0.5 ms, and the pulse interval t2 may be 50 ms (20 Hz) in moderate stimulation. In maximum stimulation, t2 is reduced to about 20 ms (50 Hz). The amplitude of the output voltage V is not affected as long as the output voltage V is above a threshold for stimulation of all fibers in the nerve. The threshold is electrode-related and amounts to about 5 volts for the electrode used here and described below.

An electrode (to be described below for the vagus nerve in conjunction with FIG. 4) in the system 23 and electrode cable for the respective nerve to be stimulated can consist of one or more flexible electrical conductors made of, e.g., MP35, each conductor being enclosed in electrical insulation made of, e.g., silicone rubber. The collective silicone rubber insulation on the conductors serves as the electrode cable's outer sheath. The electrode is devised for bipolar stimulation and has a first sub-electrode for the cathode and a second sub-electrode for the anode.

The sub-electrodes can be devised as cuffs, rings, helices or the like with e.g. platinum, and other electrically conducting metals and/or polymers, as well as carbon fibers/meshes as electrode material in contact with the nerve and an electrically insulating and mechanically resilient sheath of silicone rubber around the electrode material. The silicone rubber is pre-tensioned to some degree so that electrode, after implantation, retains mechanical and electrical contact with the nerve. The electrode can also be provided with suturing appliances and a device for mechanically relieving the load on the sub-electrodes, e.g. silicone rubber anchoring around the nerve with tensile relief for the conductors of the sub-electrodes. The electrode may also be anchored, with a constructively adapted design, in a blood vessel, preferably a venous vessel, immediately adjacent to the nerve.

A construction which is similar in all essential respects to the construction described for the stimulation electrodes can also be used for the sensor electrode employed for sensing heart-related activity in the sympathetic nerve. The vagus nerve could also be used, but the description relates to the sympathetic nerve as an example, whereby the nerve signals are sent to the nerve signal monitoring device 53 in the detection unit 5. The sensor electrode for the sympathetic nerve 26 can simultaneously serve as the stimulation electrode for the sympathetic nerve 26.

Figure 4:
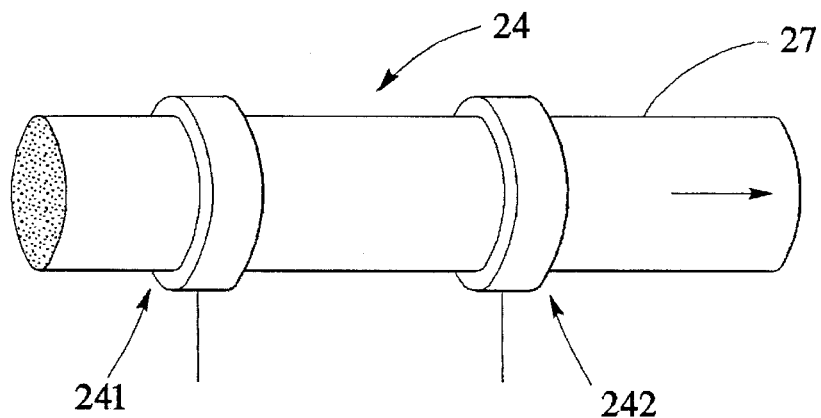
FIG. 4 shows an example of the structure of a nerve electrode suitable for use in accordance with the invention.

FIG. 4 shows an example of the construction principles for a cylindrical nerve electrode used herein and applicable to a nerve. FIG. 4 shows the vagus nerve 27 and an electrode 24, consisting of a sub-electrode 241 arranged distal to the heart and a sub-electrode 242 arranged proximal to the heart 25, arranged thereon. The arrow in FIG. 4 points toward the heart 25. The sub-electrodes 241 and 242 are for activating stimulation and are connected via conductors in the system 23 (FIG. 1) to the plus output terminal 916 and the minus output terminal 917, respectively, of the nerve stimulator 910. In case that the sub-electrode 24 leads to an anodic block, the result is that the main direction of nerve impulses is toward the heart 25.

As previously noted, the current generator 91 can also emit a current for blocking the sympathetic nerve 26, in addition to emitting the described pulses from the nerve stimulator 910 for activating the vagus nerve 27. One such blocking current can be achieved by additionally arranging, in the current generator 91, a pole-reversed nerve stimulator 910, described in FIG. 2, so the sub-electrode 242 becomes positive and so the sub-electrode 24 negative. Here, the frequency of the emitted blocking pulses should range from 200 to 500 Hz so the action potential in the nerve never has time to drop. Another way to achieve a nerve blockage is to provide the current generator 91 with a direct current generator for emitting a direct current which can be applied to the sympathetic nerve 26 as a direct current from the plus pole of the direct current generator for e.g. a few seconds. Also, instead of a direct current a square wave provided by a square wave generator can be employed.

Stimulation and any sensor electrodes for the sympathetic nerve and the vagus nerve are preferably implanted in the patient's neck area. For the vagus nerve 27, the preferred implantation site is in the neck area by or near the right middle portion of the external carotid artery. For the sympathetic nerve, the preferred implantation site, as regards stimulation, is the ganglion stellatum, whereby an electrode adapted to use with this thickened part of the nerve is employed.

The nerve-heart defibrillator described herein and including the unit 9 therefore achieves defibrillation of the heart 25 by delivering an activating current to the vagus nerve 27 and a blocking current to the sympathetic nerve 26 from the block 9 in response to one or more fibrillation conditions detected by the units 51, 52 and 53 in the detection unit 5. If the fibrillation persists, despite this treatment (which can be repeated if necessary) from the nerve-heart defibrillator unit 9, the control unit 13 can order collaboration with other parts of the defibrillator implant 1 which are relevant to the persistent fibrillation condition, so that one or more electrical defibrillation shocks are emitted by the block 11 for electrical defibrillation.

It should be noted that the nerve-heart stimulator unit 9 according to the invention in the defibrillator implant 1 is also capable of treating, as previously noted, impending but as yet unestablished fibrillation conditions (or other refractory tachyarrythmia) by prophylactically applying an activating current to the vagus nerve 27 and a blocking current to the sympathetic nerve 26, as described above.

The nerve signal monitoring device 53 contributes to improved monitoring by the detection unit 5 as regards tachyarrhythmias. The device 53 is, e.g., arranged to be able to observe changes in the signal patterns of the autonomic nervous system generated by e.g. myocardial ischemia, a condition which often precedes a tachyarrythmia. When the signal patterns are registered with an electrode as described herein (FIG. 4) and these patterns are processed (e.g. compared to patterns which are present under normal conditions), changes can be detected in sufficient time before dangerous tachyarrythmia becomes established.

One example of the course in treatment with the nerve-heart defibrillator unit 9, utilizing the neurosensor 53 and collaborating with other units in the defibrillator implant 1, is provided below.

As soon as the detector unit 5 detects impending fibrillation or some other dangerous, impending tachyrhythmia (e.g. a change in the activity of the autonomic nervous system), treatment from the unit 9 can be started in the form of light activation of the vagus nerve 27 for 5 seconds. If the detector unit 5 detects a return to a normal state of the heart 25, treatment is terminated. If the detector unit 5 continues to detect an abnormal condition for the heart 25, treatment will continue, supplemented with blocking of the sympathetic nerve, preferably at the ganglion stellatum, for a few seconds. If heart activity drops below a given rate because of the current delivered to the vagus nerve and the sympathetic nerve, the pacemaker block 7 automatically begins stimulating the heart 25 in order to maintain or restore its sinus rhythm. Treatment is terminated if the detector 5 now shows that the heart 25 has returned to a normal state. If this is not the case, the electrical defibrillator block 11 can be activated in order to shock the heart 25 in the conventional way.

Although the nerve-heart stimulator unit 9 has been described in the context of a conventional implant which also comprises many other units, the described example clearly only shows some of the therapy possibilities of the nerve-heart defibrillator 9 and shall not be interpreted as any restriction on its use. The nerve-heart stimulator unit 9 can alternatively, in treatment of supraventricular arrhythmias, only include the parts which stimulate the vagus nerve. In the treatment of supraventricular arrhythmias, the nerve-heart stimulator does not necessarily have to be implanted in the patient's body. It can also be used extracorporeally, e.g. for temporary use with appropriately situated external and internal nerve electrodes.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for detecting a condition indicative of imminent cardiac arrhythmia of a heart of a subject and for administering anti-arrhythmia therapy in response thereto, comprising:

sensor means, placeable in an extracardiac position in said subject for directly sensing nerve signals conveying information from at least one member of the autonomic nerve system, of the group consisting of the sympathetic and vagus nerves of said subject, to said heart of said subject, said sensor means generating a single sensor signal corresponding to the sensed nerve signals;

a comparator supplied with said single sensor signal and having a threshold value defining a condition indicative of an arrhythmia and said comparator emitting an output signal indicating a state of imminent arrhythmia dependent on a relation between said single sensor signal and said threshold value; and means for administering anti-arrhythmia therapy to said subject upon emission of said output signal indicating said state of imminent arrhythmia.

2. An apparatus as claimed in claim 1 wherein said sensor means comprise an electrode directly connectable with said member of the autonomic nervous system.

3. An apparatus as claimed in claim 1 wherein said member of the autonomic nervous system has a longitudinal extent, and wherein said sensor means comprise two electrodes directly connectable with said member of the autonomic nervous system and disposable a distance from each other along said longitudinal extent.

4. A method for detecting, a state of imminent cardiac arrhythmia of a heart of a subject and for administering anti-arrhythmia therapy to said subject in response thereto, comprising the steps of:

implanting a sensor in an extracardiac position in said subject and directly sensing nerve signals conveying information from at least one member of the autonomic nervous system, of the group consisting of the sympathetic and vagus nerves of said subject, to said heart of said subject, and generating a single sensor signal corresponding to the sensed nerve signals;

comparing said single sensor signal to a threshold value defining a condition indicative of an arrhythmia and emitting an output signal indicating a state of imminent arrhythmia dependent on a relationship of said single sensor signal relative to said threshold value; and administering anti-arrhythmia therapy to said subject upon emission of said output signal.

5. A method as claimed in claim 4 wherein the step of implanting said sensor comprises implanting said sensor in direct contact with said member of the autonomic nervous system.

6. A method as claimed in claim 4 wherein said member of the autonomic nervous system has a longitudinal extent, and wherein the step of implanting said sensor comprises implanting two electrodes, forming said sensor, at a distance from each other in direct contact with said member of the autonomic nervous system along said longitudinal extent.

7. An apparatus for detecting a condition indicative of imminent cardiac arrhythmia of a heart of a subject and for administering anti-arrhythmia therapy in response thereto, comprising:

nerve sensor means, placeable in an extracardiac position in said subject for directly sensing nerve signals conveying information from at least one member of the autonomic nerve system, of the group consisting of the sympathetic and vagus nerves of said subject, to said heart of said subject, said nerve sensor means generating a nerve sensor signal corresponding to the sensed nerve signals;

a comparator supplied with said nerve sensor signal and having a threshold value defining an autonomic nervous system condition indicative of an arrhythmia, said comparator emitting a comparator output signal dependent on a relationship of said nerve sensor signal relative to said threshold value;

hemodynamic sensor means, placeable relative to a blood vessel in said subject, for monitoring blood pressure in said blood vessel, said hemodynamic sensor means generating a hemodynamic sensor signal corresponding to the blood pressure;

hemodynamic signal monitoring means supplied with said hemodynamic sensor signal for analyzing said hemodynamic sensor signal relative to hemodynamic conditions indicative of an arrhythmia, said hemodynamic signal monitor emitting a hemodynamic output signal dependent on a relationship of said hemodynamic sensor signal to said hemodynamic condition;

control means, supplied with said comparator output signal and said hemodynamic output signal, for generating a control output signal indicating a state of imminent arrhythmia dependent on said comparator output signal and said hemodynamic output signal; and means for administering anti-arrhythmia therapy to said subject upon emission of said control output signal.

8. An apparatus as claimed in claim 7 wherein said sensor means comprise an electrode directly connectable with said member of the autonomic nervous system.

9. An apparatus as claimed in claim 7 wherein said member of the autonomic nervous system has a longitudinal extent, and wherein said sensor means comprise two electrodes directly connectable with said member of the autonomic nervous system and disposable a distance from each other along said longitudinal extent.

10. An apparatus as claimed in claim 7 wherein said hemodynamic sensor means comprise an annular holder part adapted for surrounding said blood vessel, and a sensor part disposed inside of said holder part.

11. An apparatus as claimed in claim 10 wherein said sensor part comprises a blood pressure-sensitive cuff.

12. A method for detecting a condition indicative of imminent cardiac arrhythmia of a heart of a subject and for administering anti-arrhythmia therapy in response thereto, comprising the steps of:

implanting a sensor in an extracardiac position in said subject and directly sensing nerve signals conveying information from at least one member of the autonomic nervous system, of the group consisting of the sympathetic and vagus nerves of said subject, to said heart of said subject, and generating a sensor signal corresponding to the sensed nerve signals;

comparing said nerve sensor signal to a threshold value defining an autonomic nervous system condition indicative of an arrhythmia, and emitting a comparator output signal dependent on a relationship of said nerve sensor signal relative to said threshold value;

implanting a hemodynamic sensor relative to a blood vessel in said subject, and monitoring blood pressure in said blood vessel, and generating a hemodynamic sensor signal corresponding to the blood pressure;

analyzing said hemodynamic sensor signal relative to hemodynamic conditions indicative of an arrhythmia, and emitting a hemodynamic output signal dependent on a relationship of said hemodynamic sensor signal to said hemodynamic condition;

generating a control output signal indicating a state of imminent arrhythmia dependent on said comparator output signal and said hemodynamic output signal; and administering anti-arrhythmia therapy to said subject upon emission of said control output signal.

13. A method as claimed in claim 12 wherein the step of implanting said sensor comprises implanting said sensor in direct contact with said member of the autonomic nervous system.

14. A method as claimed in claim 12 wherein said member of the autonomic nervous system has a longitudinal extent, and wherein the step of implanting said sensor comprises implanting two electrodes, forming said sensor, at a distance from each other in direct contact with said member of the autonomic nervous system along said longitudinal extent.

* * * * *